United States Patent [19]

Kumabe et al.

[11] Patent Number: 4,496,321
[45] Date of Patent: Jan. 29, 1985

[54] VIBRATION METHOD FOR CUTTING TEETH

[75] Inventors: Junichiro Kumabe, Tokyo, Japan; Masaru Kumabe, 1-1, Ise 4-Chome, Kofu-shi, Yamanashi, Japan

[73] Assignee: Masaru Kumabe, Kofu, Japan

[21] Appl. No.: 383,622

[22] Filed: Jun. 1, 1982

[30] Foreign Application Priority Data

Aug. 24, 1981 [JP] Japan .................. 56-132515

[51] Int. Cl.³ .................................... A61C 5/00
[52] U.S. Cl. .............................. 433/215; 433/119
[58] Field of Search ............... 433/119, 118, 120, 122, 433/123, 124, 215, 144, 114

[56] References Cited

U.S. PATENT DOCUMENTS

| | | | |
|---|---|---|---|
| 2,947,082 | 8/1960 | Epstein | 433/119 |
| 2,990,616 | 7/1961 | Balamuth et al. | 433/119 |
| 3,094,115 | 6/1963 | Polin | 433/215 |
| 3,133,351 | 5/1964 | Seggern | 433/119 |
| 3,332,149 | 7/1967 | Mumaw | 433/119 |
| 3,400,459 | 9/1968 | Stemler | 433/114 |
| 3,589,012 | 6/1971 | Richman | 433/86 |
| 3,924,335 | 12/1975 | Balamuth et al. | 433/119 |
| 3,930,173 | 12/1975 | Banko | 433/119 |
| 4,219,619 | 8/1980 | Zarow | 433/118 |

FOREIGN PATENT DOCUMENTS 36-19650 10/1961 Japan .................. 433/119

*Primary Examiner*—John J. Wilson
*Attorney, Agent, or Firm*—Robert E. Burns; Emmanuel J. Lobato; Bruce L. Adams

[57] ABSTRACT

A vibrational cutting system for a tooth is disclosed which comprises a combination of a cutting tool adapted to rotate at a high speed and having a tip which is effective to cut a tooth, and an apparatus for exciting the tooth. The apparatus excites the tooth to vibrate at a frequency which is greater than the natural frequency of the tooth. The cutting tool is operated under either condition (1) that the feed rate of the cutting tool is less than the maximum vibrational speed of the tooth, as viewed in the feed direction, or condition (2) that the depth of cut into the tooth is less than the amplitude of vibration of the tooth as excited by the apparatus.

11 Claims, 6 Drawing Figures

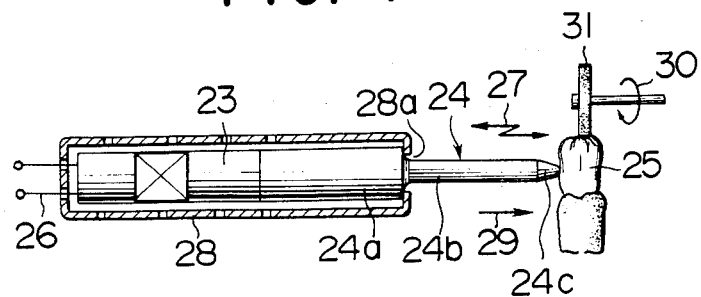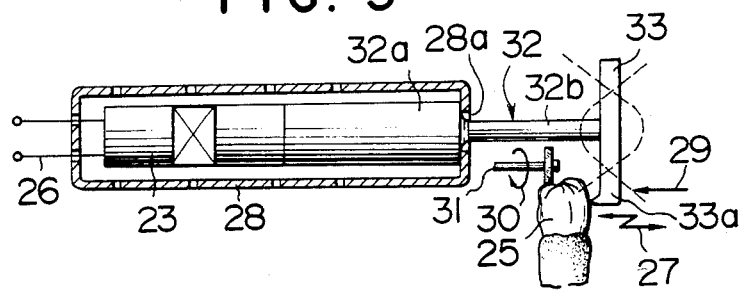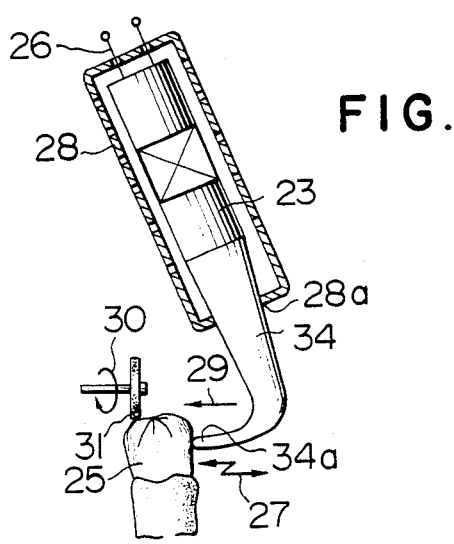

VIBRATION METHOD FOR CUTTING TEETH

FIELD OF THE INVENTION

The invention relates to a vibration cutting system for teeth, and more particularly, to a method of cutting teeth using an ultrasonic tooth exciting apparatus in cooperation with a high speed rotating cutting tool.

BACKGROUND OF THE INVENTION

A variety of cutting tools, handpieces, and contra-angle units have been devised for use in cutting a tooth in order to alleviate the discomfort, horror and pains experienced during a cutting operation. In addition, a variety of theoretical and technical developments have been made in respect of the anesthesia. Materials used for cutting tools changed from high speed tool steel to cemented carbide tool, whereby the useful life of the tools has been improved while simultaneously improving the sharpness of the cutting edge over a prolonged period of time. The shape accuracy of the cutting edge is made uniform, removing non-uniformity in the sharpness, which reduces a variation in the magnitude of force required for the cutting operation. The machining accuracy of various parts including the handpiece and contra-angle has also been improved. This resulted in an improvement in the accuracy of rotation of the rotating parts, minimizing a deflection of the rotating axis. Improvement in the machining and the assembling accuracy of ball bearings enables a high speed rotation on the order of 300,000 to 500,000 revolutions per minute. The development of a cutting tool utilizing diamond made it possible to reduce the cutting force required, as a result of a high speed cutting. An analysis of human engineering with respect to the unit construction covers a detailed examination of the workability, stability and the color which contributes to reducing the uneasiness, bringing forth a substantial improvement in the performance and the functionability.

Despite the various efforts made, there remains the discomfort, horror and pains experienced during the cutting of teeth. Since this is a mechanical cutting of teeth with a cutting tool, any effort to reduce the mechanical force required, to suppress dynamic behaviour of the teeth during the cutting operation and to eliminate dynamic stimulus factors applied to the nerves will be one way of alleviating the pains experienced. Therefore, the procedure to alleviate the pains will be (1) fixing the teeth, (2) reducing the cutting force required, and (3) the use of anesthesia. To fix the teeth, the bridge process which utilizes adjacent teeth is known. However, because a troublesome preparation is required to effect the bridge process, little use is made of this technique in practice. The step (2) can be challenged by utilizing a diamond tool having an improved sharpness. This brings forth a degree of desired effect in reducing the cutting force required, minimizing the dynamic bahavior of the teeth and alleviating the pains. However, a patient is still obliged to suffer the normal discomfort, horror and pains associated with tooth cutting. Consequently, when required, the step (3) is utilized by the injection of a narcotic or the use of laughing gas to remove pains. However, recently, the use of ordinary anesthesia is frequently forbidden for reasons of medicine shocks. If the use of anesthesia is permitted, an increased length of time is required for recovery. Hence, it will be seen that it will be desirable to achieve the cutting of teeth without suffering from the discomfort, horror and pains while avoiding the use of anesthesia.

DESCRIPTION OF THE PRIOR ART

Japanese Pat. No. 296,443, published Oct. 17, 1961 discloses that a significant reduction in the pains suffered, as compared with the cutting through a usual high speed rotation, can be achieved by a vibratory cutting of teeth in a manner such that a pulsating cutting force waveform appears. In this Japanese Patent, a torsional ultrasonic vibration having a frequency of f and an amplitude a is applied to a cutting tool which is then subjected to a high speed rotation with a cutting speed V, which is chosen to be less than $2\pi af$. However, when the cutting tool is to satisfy such requirements, its grip must be increased in size, presenting difficulty in implementing a precise cutting operation by hand. This limited its use to cutting anterior teeth and dental technician works. The application of the ultrasonic technology in the dental field is found in U.S. Pat. Nos. 3,589,012, 3,651,576, 3,924,335, 4,110,908 and 4,229,168. However, these represent the application to a scaler, massager, cleaner and contra-angle, and present little contribution to the field of tooth cutting.

The vibratory cutting theory based on the pulsating cutting force waveform is known presently in the field of mechanical precision working. Briefly, referring to FIG. 1 which illustrates the principle of operation, in a two-dimensional metal working, a workpiece 100 is shown moving with a cutting speed v. A cutting tool 101 is caused to vibrate in the same direction as the cutting direction indicated by an arrow 105, with a frequency f and an amplitude a. When the cutting speed v is chosen such that $v < 2\pi af$, there are produced pulsating cutting force waveforms 106, 107 as indicated on the right-hand side of FIG. 1. Thus, the cutting edge of the tool 101 initiates vibration at an origin O, and produces a swarf 102 during a cutting time tc associated with an arc $\overarc{EFA}$. At point A where the speed of vibration is equal, the swarf 102 begins to move away from the relieved surface of the tool, and after time $t_2$ referenced to the origin O, the tool begins to engage another swarf 103, producing a fresh swarf 104 during a cutting time tc associated with an arc $\overarc{BGD}$. Thus, it will be seen that the cutting force is effective only during the time tc and is ineffective otherwise. In this manner, pulsating cutting force waveforms are produced in succession. When the cutting speed v is increased to a value where $v = 2\pi af$, the pulsating cutting force waveforms disappear and is replaced by a conventional waveform including a high speed cutting force waveform $P + p \sin \omega t$. The pulsating cutting force waveform can be mathematically expressed as follows:

$$P(t) = \frac{tc}{T} P + \frac{2}{\pi} P \sum_{n=1}^{\infty} \frac{1}{n} \sin n \frac{tc}{T} \pi \cos n \omega t$$

The dynamic behaviour of a horizontal displacement x of a workpiece which is subject to an elastic oscillation when the pulsating cutting force waveform is applied thereto will be analyzed for a turning operation illustrated in FIG. 2. An equation of motion for the horizontal displacement x of a workpiece 110 can be written as follows:

$$M\frac{d^2x}{dt^2} + C\frac{dx}{dt} + Kx = P_t(t)$$

where M represents the mass of the workpiece, C a dashpot constant and K a spring constant. Consequently, $$M\frac{d^2x}{dt^2} + C\frac{dx}{dt} + Kx = \frac{tc}{T}P_t + \frac{2}{\pi}P_t\sum_{n=1}^{\infty}\frac{1}{n}\sin n\frac{tc}{T}\pi \cos n\omega t \quad (1)$$

The dynamic displacement x of the workpiece will be therefore as follows:

$$x = \frac{tc}{T}\cdot\frac{P_t}{K} + \sum_{n=1}^{\infty}\frac{\frac{P_t}{K}\cdot\frac{2}{n\pi}\sin n\frac{tc}{T}\pi}{\sqrt{\left(1 - n^2\frac{\omega^2}{\omega_n^2}\right)^2 + 4n^2\nu^2\frac{\omega^2}{\omega_n^2}}}$$

where $$\psi_n = \tan^{-1}\frac{1 - n^2\frac{\omega^2}{\omega_n^2}}{2n\nu\frac{\omega}{\omega_n}}$$

When the horizontal angular natural frequency $\omega_n$ of the workpiece 110 is less than the angular natural frequency $\omega$ of a cutting tool 111, or $\omega_n(=2\pi fn) << \omega(=2\pi f)$, we have $$x \doteq \frac{tc}{T}\cdot\frac{P_t}{K} \quad (2)$$

If a forced oscillation of the tool 111 having the frequency f and the amplitude a is suppressed to allow the workpiece 110 to rotate at a high speed to establish a conventional high speed cutting condition, the cutting force waveform then will be represented by $P_t + pt \sin \omega t$. Hence, the equation of motion for the horizontal displacement x of the workpiece will be as follows:

$$M\frac{d^2x}{dt^2} + C\frac{dx}{dt} + Kx = P_t = pt \sin \omega t \quad (3)$$

In the above equation, when the horizontal angular natural frequency $\omega_n$ of the workpiece is less than the angular natural frequency $\omega$ of the cutting force waveform or $\omega_n(=2\pi fn) << \omega(=2\pi f)$, we have $$x \doteq \frac{P_t}{K} \quad (4)$$

It will be noted that both equations (2) and (4) do not include the time as a variable. In other words, the workpiece does not oscillate with time, but is merely displaced from the origin O, which represents the center of rotation prior to the turning operation, by an amount which corresponds to the static displacement represented by either equation (2) or (4). If a conventional low speed cutting operation is employed, the equation (4) is reduced to $X = (P_t/K) + X(t)$, and it is seen that the workpiece greatly oscillates with time, degrading the machining accuracy. It will be noted that the necessity for a high speed operation is to make the workpiece static as indicated by the equation (4). It is one aspect of the invention to apply this fact to the cutting operation of teeth. The pulsating cutting force waveform is applied for purpose of performing a cutting operation since the workpiece is then displaced by a small amount to the condition represented by the equation (2) in which the displacement is reduced than that of the equation (4) by a factor $(tc/T(\doteq \frac{1}{3} \sim 1/10))$, thus achieving a static effect.

A close examination of an equivalent model of a machining operation with a lathe shown in FIG. 2 will reveal that a spring k and a dashpot C correspond to the region of alveolo-dental membrane present between the alveolar bone and the teeth, and that the workpiece 110 corresponds to a tooth. Consequently, by performing a high speed cutting operation through a high speed rotation of the cutting tool on the basis of the physical significance of the equation (4), the displacement x of the tooth then exhibits little oscillation, thus alleviating the pains in a corresponding manner. This represents a high speed tooth cutting technique which utilizes a diamond tool which achieves as high as 300,000 to 550,000 revolutions per minute rotation such as are in use at the present time. However, an investigation by the inventors reveal that the high speed cutting effect as indicated by the equation (4) of the tooth cannot be realized if the high speed cutting technique is implemented without the use of anesthesia, unless the number of revolutions of the tool is increased by an order of magnitude. Accordingly, with a high speed rotation in such range of the number of revolutions, there will be a cutting tone of a high pitch, and the heat produced by the friction reduces the useful life of the cutting tool. In addition, the sharpness is liable to change, causing a fluctuation in the magnitude of the cutting force P. This causes an irregular displacement of the tooth, which in turn causes pains to be experienced. Therefore, a frequent adjustment of the rotational accuracy of the rotating parts of the handpiece or contra-angle or a frequent replacement of the cutting tool is required, and the anesthesia is unavoidably used under certain instances while the degree of pains is constantly observed. On the other hand, as indicated by the equation (2), the displacement x of the tooth during a vibratory cutting operation is given as follows:

$$x \doteq \frac{\frac{tc}{T}\cdot P_t}{K} \quad (5)$$

Thus, even assuming that the cutting force $P_t$ is equal during a conventional high speed operation under the same conditions, in terms of a region of the tooth to be worked, a feed rate and a configuration of a tool, as when the vibratory cutting operation is utilized (even though the magnitude of $P_t$ during the vibratory cutting operation is reduced in practice), the apparent cutting force which influences the displacement x of the tooth will be $(tc/T)P_t\{(\frac{1}{3} \sim 1/10)P_t\}$ as indicated by the equation (5), thus drastically reducing the cutting force as compared with a conventional practice. It is found that the vibratory cutting operation of a tooth in which a pulse-like cutting force waveform is applied to the tooth which is subject to an elastic oscillation reduces the pains experienced, as compared with the conventional high speed cutting operation. Based on this finding, Japanese Pat. No. 296,443 cited above has proposed a method of cutting a tooth comprising the steps of subjecting a cutting tool to a torsional ultrasonic vibration with a frequency f and an amplitude a, and rotating the tool so that its cutting speed V is less than $2\pi af$. However, a tooth cutting device which is used to carry out the method required a grip of an increased size, which prevented its practical use.

SUMMARY OF THE INVENTION

It is an object of the invention to provide a novel system for cutting a tooth without substantially causing any pain to a patient.

It is another object of the invention to provide a method of cutting teeth using a tooth exciting apparatus in cooperation with a high speed rotating cutting tool of a known form.

In accordance with the invention, there is provided a vibratory cutting system for teeth which is formed by a combination of a tooth cutting tool having a tip which rotates at a high speed for cutting a tooth, and a tooth exciting apparatus which is disposed in contact with a tooth for exciting it. The apparatus comprises a cylindrical housing having a front opening, an acoustic transducer disposed within the housing for producing vibration energy of a predetermined frequency, a vibration transmitting member including a rear section disposed within the housing and having its end coupled to the acoustic transducer and a front section which extends outwardly through the opening formed in the housing and having its free end disposed for contact with a tooth, support means for securing a vibrator formed by the combination of the acoustic transducer and the transmitting member to the housing at a point of balance thereof, and electrical means for feeding electric power to the acoustic transducer. The acoustic transducer has an oscillation frequency which is higher than the natural frequency of the tooth, and excites the free end of the front section of the transmitting member so that the amplitude at the free end is 30 μm at maximum or less. The system is operated under either condition (1) that the feed speed s of the cutting tool is related to the maximum vibrational speed $2\pi af$ of the tooth, as viewed in the feed direction, such that $s < 2\pi af$, where a represents the amplitude as measured at the free end of the transmitting member, and f the oscillation frequency of the transducer, or condition (2) that the depth of cut, t, into the tooth of the cutting tool is related to the amplitude a such that $t < a$. Preferably, the acoustic transducer comprises an ultrasonic transducer which produces high vibrational energy in the ultrasonic range.

In accordance with the invention, the vibrational energy supplied to the tooth from the ultrasonic transducer through the transmitting member causes the apparent spring constant thereof to be increased to a high value, whereby the tooth is constrained in a manner equivalent to its being fixed in a stationary condition. A cutting operation takes place under this condition so that the cutting tool produces a pulse-like cutting force waveform, and a dental therapy can be accomplished without imparting any substantial pain to a patient.

Before describing the invention in detail, a summary of the theoretical background of the invention will be in order. As a result of a fundamental research in the technique of alleviating pains experienced during the cutting of teeth, the inventor has successfully formed a model of a pain transmitting system which will be produced when cutting with a cutting tool a tooth which is coupled to the alveolar bone through the alveolo-dental membrane and comprising a cement, dentin, dental pulp and enamel body. FIG. 3 illustrates such a model. Specifically, secured to an alveolar bone 1 through a spring 2 having a spring constant k and a dashpot 3, both of which represent the alveolo-dental membrane, is a tooth having a mass M which is surrounded by a cement 4 and an enamel body 11. Interposed between the enamel body 11 and a dentin 5 are Tomes' fibers 9 and dentinal cells 8, carried by tooth fluid 10 within dentinal tubules and which are supported by a group of nerve fibers of the dental pulp through a spring 6 having a spring constant K and a dashpot 7 having a viscous attenuation coefficient C. Consequently, a static or dynamic displacement of the Tomes' fibers 9 and dentinal cells/fiber cells 8 cause a strain in the spring 6 of the nerve fibers of the dental pulp. The magnitude of the strain can be measured by a receiver 13 of the nerve system, which corresponds to a strain gauge. The strain can be amplified by an amplifier 15 having a frequency response and is then recorded on a recording paper 17 associated with a recorder 16. It is considered that the height of the resulting waveform is proportional to the degree of pains suffered in the dental pulp. On the other hand, a displacement of the spring 2 can be measured by a strain gauge which corresponds to a group of nerves distributed in the alveolo-dental membrane, thus determining the strain in the spring 2. The magnitude of such strain may be amplified by an amplifier 14 having a frequency response and then recorded on the recording paper 17. It is considered that the height of the resulting waveform is proportional to the degree of pains suffered by the group of nerves in the alveolo-dental membrane. It will be seen that this creative model permits a pattern recognition of the waveform recorded, with the understanding that the degree of pains suffered is proportional to the height of the waveform. In this manner, the pains suffered can be alleviated by attempting to reduce the height of the peaks in the recorded waveform. When cutting a tooth with a cutting tool 19, it will be seen that a deflection of a recording pen in the recorder will be zero and hence the recorded waveform remains linear or the pains will be completely eliminated if no strain is caused in the spring 2 of the alveolo-dental membrane and the spring 6 of the dental pulp. This is equivalent to a tooth cutting when the pulp and hence the spring 6 is removed, and the tooth is secured to the alveolar bone, thus completely eliminating any change in the spring 2.

In general, a tooth being cut suffers from a variety of inflammations in the alveolo-dental membrane, and hence the spring is strained as a result of either elongation or shrinkage as compared with the spring condition of a balanced and strain-free, sound tooth. Consequently, the waveform recorded on the recording paper undergoes a periodic undulation, and a patient undergoes suffering from stinging pains. An intense pain will be felt as a result of a probing which applies a very slight magnitude of external force. Fixing this tooth by utilizing the bridge process which is applied across adjacent teeth may involve a contact with the tooth in question, causing an intense pain to be experienced. Thus, it is evident that a reduction in the magnitude of the cutting force is the very first means which must be considered in order to alleviate the pains. When the cutting edge of the tool directly contacts the tooth in question to apply force thereto according to Newton's law, the application of the pulsating cutting force waveform as understood according to the present cutting theory and technology is unable to reduce the displacement of the tooth or the spring 2 to zero even though such displacement is greatly reduced as indicated by the equation (2). Considering a case in which the spring 2 in the alveolo-dental membrane is sound, but the spring 6 in the dental pulp suffers from a variety of inflammations to produce either elongation or shrinkage and thus is strained, the waveform recorded on the recording paper undergoes a periodic undulation, and the patient is suffering from stinging pains. Initiating the cutting operation from the enamel body on the surface of the tooth, intense pains will be momentarily felt in the region of the boundary with the dentin if the tooth itself or the spring 2 is stationary as when the tooth is fixed. This can be explained as a result of an elastic displacement or oscillation of the spring 6 which is caused by a dynamic displacement of the Tomes' fibers 9, representing a group of small masses situated within the tooth fluid 10, produced by a flow of the fluid and the application of the cutting force, as well as by a dynamic displacement of the dentinal cells/fiber cells 8 produced by the application of the cutting force. To alleviate the resulting pains, it is inferably understood from FIG. 3 that the elastic displacement or oscillation of the spring 6 must be minimized. Since it is the very purpose to minimize the elastic displacement or oscillation of the fiber cells 8 and the Tomes' fibers 9, it will be seen that the application of the pulsating cutting force waveform as represented by the equation (2) to perform a cutting operation is the best way. Nevertheless a small degree of static displacement of the spring 6 is unavoidable. Resort must be had to the injection of a narcotic or the use of laughing gas if the pains cannot be endured though the best way of reducing the cutting force is employed. Referring to FIG. 3, the use of anesthesia is equivalent to interrupting the circuit connection with the amplifiers 14, 15 in the pain transmitting circuit shown in FIG. 3, thus preventing any signal from being fed to the recorder 16. The use of laughing gas is equivalent to interrupting the circuit connection around the recorder 16, again preventing any pain signal from being recorded.

To determine a specific technique which further reduces the cutting force, an experiment has been made. Block samples of ceramic materials including magnesia (Mohr's hardness 6) mullite (Mohr's hardness 7), zirconia (Mohr's hardness 8) and alumina (Mohr's hardness 9) have been adhesively secured, by utilizing epoxy resin, to the free end of an amplitude magnifying horn which is subject to an ultrasonic oscillation at a frequency of 20 kHz and with an amplitude of 8 $\mu$m. A diamond tool having a diameter of 1 mm is pressed against the sample under a constant load of 0.4 N (40 gf). By utilizing a combination of an electric motor and an air turbine, the tool is driven with a number of revolutions which changes from 10,000 to 300,000 rpm. When the direction of the load applied coincides with the direction of vibration, the depth h $\mu$m of a dimple produced is determined. For alumina with a rotation of 30,000 rpm, h=500 $\mu$m. The value of h tends to increase in proportion to an increase in the number of revolutions of the tool and the load applied. When the number of revolutions is increased by a factor of approximately four, the depth of the dimple h increases by a factor of about two, which appears to be characteristic of hard and brittle materials. If an ultrasonic vibration of the ceramic sample is suppressed while allowing the rotation of the diamond tool alone in a conventional manner, there results a shallow dimple having h=200 $\mu$m. The ultrasonic vibration of the ceramic samples causes the depth of the dimple formed or the magnitude of the work applied to be increased as high as 2.5 times or greater than that of a conventional cutting which does not utilize the ultrasonic vibration of the ceramic member. The fact that the depth of work applied increases for the same load applied means that the resistance to the cutting work is reduced. If such result is attempted to be realized by merely increasing the number of revolutions, there is required as high a number of revolutions as 900,000 rpm, which cannot be achieved with an air turbine technique having the upper limit on the order of 550,000 rpm. The ultrasonic vibration of the ceramic sample drastically improves the sharpness of the diamond tool at the currently available number of revolutions. If the same sharpness is to be maintained, the number of revolutions can be reduced from 300,000 to 10,000 rpm. Since the useful life of the tool is proportional to the cutting speed, this means that the useful life of the tool can be increased. Thus, it is found that the ultrasonic vibration of a hard and brittle material improves the sharpness of a cutting tool or increases the useful life of the tool.

An ivory sample which is assumed to exhibit a uniform quality is subject to an ultrasonic vibration at a frequency of 28 kHz and with an amplitude of 8 $\mu$m. A diamond tool having a diameter of 1 mm and rotating at 30,000 rpm is urged against the sample with a load of 0.9N (90 gf) for a given time interval. As compared with the result achieved with a conventional high speed rotation, the depth of depression formed (h $\mu$m) increases by a factor of about 2.5 to 5, although it slightly depends on the direction of fibers of the ivory. Thus unexpected results are obtained with ivory as with ceramics. Similarly, various teeth removed from the physical body have been adhesively secured to the free end of a horn which is subject to an ultrasonic longitudinal vibration at a frequency of 28 kHz and with an amplitude of 8 $\mu$m, by means of Araldite. A diamond tool having a diameter of 1 mm and rotating at a number of revolutions of 300,000 rpm is urged against each tooth removed, with a constant load of 0.9N (90 gf) for a given time interval. As compared with the conventional cutting technique which does not utilize the ultrasonic vibration, the depth of a dimple formed increases in the similar manner as found with a ceramics and ivory. Thus the use of the ultrasonic vibration has increased the depth by a factor of about 2 to 6 as compared with the high speed rotation technique. In other words, the resistance to the cutting operation is reduced by a factor of 2 to 6. This may be attributable to a reduction in the mechanical strength, for example, the tensile strength, of the tooth itself which is produced by stresses and strains resulting from the ultrasonic vibration which influence upon the cutting mechanism of a hard and brittle material such as the apparent tooth structure present during a cutting operation.

In applying the invention to the actual teeth, a method of driving a tooth, which is coupled to the alveolar bone through the alveolo-dental membrane, for ultrasonic vibration will now be described. The natural frequency fn of a tooth is calculated based on the mass M of the tooth and the spring constant k of the spring 2 in the alveolo-dental membrane. By measurement, it has a value between 300 and 2,000 Hz. Accordingly, the tooth is excited for oscillation or vibration at a frequency greater than this fn value. A drive horn 21 is caused to oscillate in a direction indicated by an arrow 22 at a high frequency which is in the ultrasonic range, and is gently pressed against the tooth as indicated by an arrow A, whereby the tooth may be subjected to an ultrasonic vibration at the frequency f of the horn 21 and with a sinusoidal waveform having an amplitude close to the amplitude a of the horn. By way of example, the ultrasonic vibration of the tooth may take place with f=65 kHz and a=4 μm. A diamond tool 19 which undergoes a high speed rotation is applied to the tooth in a direction indicated by an arrow 20, with a substantially constant feed rate S, even though a degree of variation in the feed rate is unavoidable because of the manual operation. By choosing the feed rate S and the maximum vibrational speed $2\pi af$ of the tooth, as viewed in the feed direction, such that $S < 2\pi af$ and choosing the depth of cut, t, of the cutting tool which is related to the amplitude such that $t < a$, there is provided a cutting mechanism which regularly and periodically undergoes contact and disengagement between the rotating tool and the tooth so as to make intermittent pressure contact with the tooth, effectively producing a pulsating cutting force waveform. Thus, analyzing the feed direction of the cutting tool in the sense of a vector with respect to the direction in which the tooth is excited, the first mentioned inequality applies when the feed direction is aligned with a component of excitement of the tooth while the second mentioned inequality applies when the feed direction is orthogonal to the direction in which the tooth is excited. In this manner, the displacement can be reduced to (tc)/T·P/K as indicated in the equation (2), and the cutting force can be reliably reduced by a factor of (tc)/T, for example, ⅛ to 1/20, as compared with the cutting force P which will be produced with the conventional high speed rotation alone without incorporating the present invention.

It is generally known that when a strain gauge is adhesively coupled to a sample of an elastic material which undergoes a vibration at a high frequency as in the ultrasonic range, and a change in the voltage which results from a change in the resistance of the strain gauge is amplified by an amplifier for recording on a recording paper associated with a recorder in order to determine the frequency and/or amplitude of the vibration of the sample, an accurate indication or recording may be prevented and the indication or record may be less than the actual amplitude of vibration if the amplifier, the indicator or the recorder has a poor frequency response. This may be understood if one considers that an a.c. ammeter for 50 Hz cannot be used to provide an accurate determination of the absolute value of a high frequency current. In using an electromagnetic oscillograph, if a galvanometer having a natural frequency which is as low as 500 Hz is used to record an ultrasonic current of 20 kHz on a recording paper, a recording pen will produce no displacement which is proportional to the current flow, but remains on a point which corresponds to the origin. A similar phenomenon also occurs in the pain transmitting system illustrated in FIG. 3. Specifically, if a detector corresponding to a strain gauge is used to detect the mode of vibration of a tooth which undergoes a vibration at a frequency of 60 kHz and an amplitude of 4 μm, in combination with an amplifier corresponding to a sensory nerve and a recorder corresponding to a sensorium, both of which have a poor frequency response, there is little movement of a recording pen which occurs in proportion to the mode of vibration of the tooth, but the pen remains substantially stationary, producing no plot on the recording paper. In other words, if the tooth is statically displaced by 8 μm, there occurs a perception of pains, but when the tooth is subjected to a ultrasonic vibration at a frequency of 60 kHz and with an amplitude of 4 μm, the resulting displacement cannot be sensed and hence no pain is perceived. Such effect is virtually equivalent to the anesthesia effect as achieved by the injection of narcotic or the use of laughing gas, and will be hereafter referred to as "dynamic anesthesia".

As mentioned previously, the natural frequency of a tooth lies in a range from about 300 to 2,000 Hz. Assuming that the frequency of the ultrasonic vibration applied in accordance with the invention is 60 kHz, for example, the tooth will vibrate at this frequency, which means that the apparent natural frequency of the tooth increases during its cutting operation. There is a relationship that $\omega_n = \sqrt{k/M}$ where $\omega_n$ represents the angular natural frequency of the tooth, k the spring constant of the alveolo-dental membrane and M the mass of the tooth. Assuming that the natural frequency of the tooth which is to be treated is equal to 600 Hz, it then follows that the spring constant has been apparently rigidified or increased by a factor of 60,000/600÷100 or approximately 10,000. In other words, the apparent spring constant of the tooth is rigidified to a value which is approximately 10,000 greater than the inherent spring constant when the vibrational energy from an ultrasonic oscillator is supplied thereto. Stated differently, the vibratory driving waveform applied to the tooth is equivalent to fixing the teeth according to the conventional bridge process to permit the teeth to be cut while it remains stationary. A rounded tip of a drive horn, which oscillates at a longitudinal frequency of 60 kHz and with an amplitude of 4 μm and producing an output of 20 W, is gently applied against a tooth being cut for causing an ultrasonic vibration thereof. A diamond tool having a diameter of 1 mm is rotated at a high rate of 300,000 rpm, and is fed under a reduced pressure against a tooth which undergoes ultrasonic vibration, generally in a cutting direction. This applies a pulsating cutting force waveform, reducing the cutting force which gives rise to a dynamic displacement of the tooth which causes pains, and also drastically reducing the cutting force by utilizing the dynamic response of the tooth vibrating system. In this manner, the mode of ultrasonic vibration of the tooth which is driven by a small output on the order of 20 W is not disturbed, but the regular ultrasonic vibration is maintained while increasing the apparent spring constant to establish a dynamic anesthesia effect. In this manner, the pains otherwise suffered during a cutting operation of the tooth are drastically reduced or entirely eliminated. It is necessary that a dynamic displacement of a tooth which is caused by the cutting force remains within the magnitude of the amplitude of the ultrasonic vibration, which is 4 μm in this example. For general cutting operations, the value of amplitude 4 to 10 μm is satisfactory. If the magnitude of a cutting force becomes excessive, the ultrasonic vibration of the tooth may be impeded, reducing the amplitude. If the amplitude reduces to zero, the effect of the invention disappears. In such instance, it is necessary to recover the regular ultrasonic vibration of a tooth by increasing the output or the amplitude.

BRIEF DESCRIPTION OF THE DRAWINGS

FIGS. 4, 5 and 6 are schematic side elevations, partly in section, of a tooth exciting apparatus according to several embodiments of the invention.

DESCRIPTION OF PREFERRED EMBODIMENTS

Figure 1:
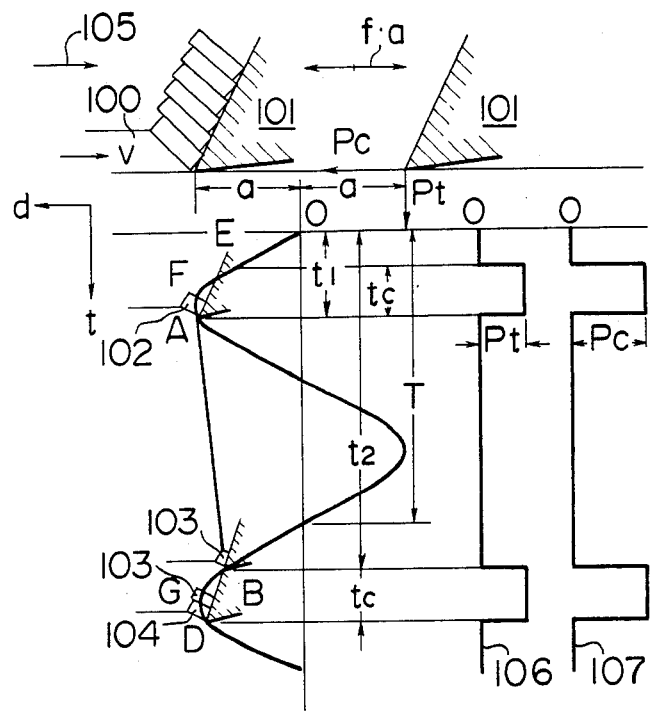
FIG. 1 is a schematic illustration of the principle of a vibration cutting technique as applied to a two-dimensional cutting operation of a metal workpiece.
Figure 2:
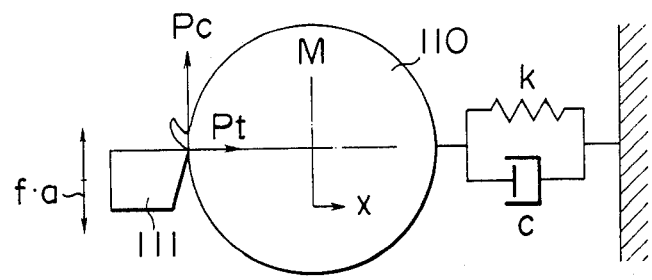
FIG. 2 schematically shows an equivalent model of a vibration cutting operation by a lathe.

As will be apparent from the foregoing description, the vibration cutting system for teeth according to the invention can be implemented by utilizing a tooth cutting tool of a known form which rotates at a high speed and a tooth exciting apparatus proposed according to the invention. The cutting tool is well known and hence requires no detailed description herein. Accordingly, only the tooth exciting apparatus or instrument will be described in detail. In several embodiments to be described below, substantially equivalent parts are designated by like reference numerals or characters.

FIG. 4 illustrates the use of an ultrasonic longitudinal vibrator 23, and a horn probe 24 which is also adapted to undergo ultrasonic longitudinal vibration and having a length designed for resonance at the frequency of the vibrator 23. The vibrator 23 may be formed as an electrostrictive or magnetostrictive vibrator, and may have an oscillation frequency greater than 20 kHz or in the ultrasonic range. The use of such high frequency enables the tooth exciting apparatus of the invention to be reduced in weight and size. The horn probe 24 may be formed of a metal rod, or may sometimes comprise a non-metal rod which is subject to an elastic deformation. The horn vibrator 24 includes a rear section 24a which is coupled to the vibrator 23 and a front section 24b including a free end 24c. Since the free end 24c is to be brought into contact with a tooth 25 for causing a vibration thereof without cutting any portion thereof, the free end is rounded so as to prevent the tooth surface from being damaged. Sometimes, the free end may have a curved surface for facial contact with the tooth in order to stabilize the contact therebetween. Because the free end of the horn probe is not abraded in contradistinction to a cutting tool, there is no need to change it, and hence it may be fabricated in an integral manner with the horn 24a. Different diameters may be required depending on the applications. Hence the front section 24b may be fabricated separate from the horn 24a and may be coupled therewith by threadable engagement or a tapered coupling. The exciting apparatus includes a pair of terminals 26, which may be connected across output terminals of an ultrasonic oscillator. Thereupon, the free end of the probe 24b undergoes ultrasonic vibration in a direction indicated by a double-ended arrow 27. A grip 28 is disposed on a node of vibration of the horn 24a. The vibrator 23 and the rear section 24a of the horn probe 24 are contained within the grip 28, and the front section 24a projects forwardly through a opening 28a formed in the grip 28. By holding the grip with the hand, the free end 24c of the horn probe 24 may be gently pressed against the tooth 25, as indicated by an arrow 29 to cause a vibration of the tooth, which is then subjected to a cutting operation by a cutting tool 31, such as a diamond grinder, which rotates at a high speed as indicated by an arrow 30.

Where the front side of the tooth 25 is capped with a metal crown, it may be necessary to apply the horn probe 24 against the rear surface of the tooth where the crown is absent, since the presence of a metal crown may interfere with the transmission of the vibrating drive. FIG. 5 shows an apparatus which may be used in such instance. Specifically, it comprises an ultrasonic longitudinal vibrator 23, a longitudinal vibrating horn 32 having a length chosen for resonance at the frequency of the vibrator 23, and a probe 33 shaped for bending resonance and attached to the free end of the horn 32 at an antinode thereof. On its free end which corresponds to an antinode, the probe 33 is provided with a projection 33a which is rounded in the same manner as the free end of the horn probe 24 shown in FIG. 4. The projection 33a undergoes ultrasonic vibration in a direction indicated by an arrow 27. The probe is pressed against a tooth as indicated by an arrow 29 to cause a vibration thereof, while the tooth 25 is subject to a cutting operation by a cutting tool which rotates at a high speed. As shown, the horn 32 includes a rear section 32a having its end coupled to the vibrator 23 and a front section 32b having the probe 33 attached to its end.

FIG. 6 shows a tooth exciting apparatus comprising a longitudinal vibrator and a curved horn probe 34 which is operative to magnify the amplitude. The probe 34 has a tip 34a which is adapted to vibrate in a direction indicated by an arrow 27. When the tip is gently pressed against the tooth 25 as indicated by an arrow 29 to cause a vibration thereof, the latter may be cut by a cutting tool which rotates at a high speed.

If a high speed rotation alone is relied upon as may be obtained by the use of a conventional air turbine, any slight reduction in the sharpness of the tool resulted in the occurrence of discomfort and pains. This determines the useful life of the tool, which therefore had to be frequently changed. However, with the present invention, the useful life of a tool can be increased by a factor of 3 to 10. Since the pulsating cutting force waveform is applied, the heat produced during a tooth cutting operation has also a pulsating cutting force, and a frequency response appears in a heat transmission system in the similar manner as the frequency response of a dynamical system, thus drastically reducing the pains suffered due to the heat produced. With the present invention, teeth which had to be treated heretofore by the use of anesthesia can be machined while avoiding the anesthesia, without causing pains, discomfort or horror. This is particularly effective when the use of anesthesia must be avoided for reason of medicine shock. Another advantage is a substantial reduction in the amount of sound produced during a cutting operation, which has a psychological effect.

The effects of the invention can be demonstrated by specific results:

(1) A cavity can be formed in an ideal manner according to the invention for a patient who suffers from erethism of dentin perception and who feels pains when a tooth is touched by a probe.

(2) The invention can be applied to a tooth having $C_3$ caries degree 3 and suffering from pains upon impacting, successfully cutting the dental pulp to the top thereof in indolence.

(3) A cutting operation has been successfully achieved without anesthesia for teeth which suffer from acute purulent inflammation of aveolo-dental membrane, chronic ulcerate inflammation of dental pulp, necrosis of dental pulp, partial acute purulent inflammation of dental pulp, etc.

Figure 3:
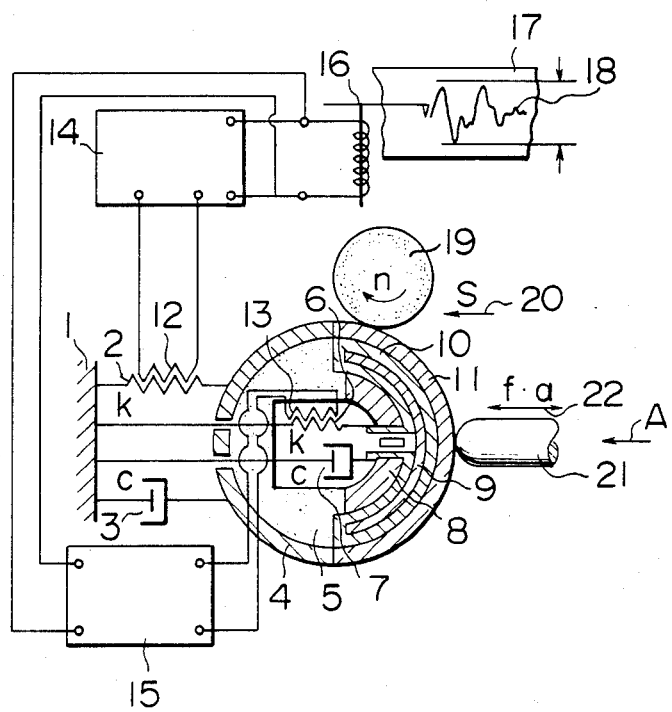
FIG. 3 schematically shows an equivalent model of a vibration cutting operation of a tooth according to the invention.

As will be noted from the model shown in FIG. 3, in addition to the cutting force intentionally applied, the springs 2 and 6 may be subject to elongation or shrinkage for various reasons such as by inflammation in its surrounding region to cause an expansion of the springs. When strains are produced in this manner to cause stinging pains, the drive horn of the invention may be applied against the tooth in question, and an ultrasonic vibration may be applied thereto having an amplitude which corresponds to the magnitude of the strains, thus relieving the pains.

While the invention has been described above as utilizing an ultrasonic vibration having a frequency equal to or greater than 20 kHz which is in the ultrasonic range, the invention can be effectively applied with an equal result by utilizing a high frequency which is equal to or greater than about three times the natural frequency of the tooth.

What is claimed is:

1. A method of cutting a tooth with a cutting tool having a tip which rotates at a high speed, comprising the steps of: exciting a tooth to be cut for vibration at a frequency which is greater than the natural frequency of the tooth, bringing the cutting tool into contact with the vibrationally-excited tooth to be cut under a suitable pressure, and operating the cutting tool such that the feed rate of the cutting tool is less than the maximum vibrational speed of the tooth, as viewed in the feed direction, to effect cutting of the tooth.

2. A method of cutting a tooth with a cutting tool having a tip which rotates at a high speed, comprising the steps of: exciting a tooth to be cut for vibration at a frequency which is greater than the natural frequency of the tooth, bringing the cutting tool into contact with the vibrationally-excited tooth to be cut under a suitable pressure, and operating the cutting tool such that the depth of cut into the tooth of the cutting tool is less than the amplitude of vibration of the tooth.

3. A method of cutting a tooth with a rotary cutting tool, comprising the steps of: providing a handheld high-speed rotary cutting tool having a rotary cutting tip; exciting a tooth to be cut to effect vibration of the tooth at a frequency greater than the natural frequency of the tooth; bringing the rotary cutting tip into pressure contact with the vibrationally-excited tooth; and controlling the operation of the cutting tool to cause the high-speed rotating cutting tip to make intermittent pressure contact with the vibrationally-excited tooth to thereby apply a pulsating cutting force thereto effective to effect cutting of the tooth.

4. A method of cutting a tooth according to claim 3; wherein the exciting step comprises exciting the tooth to vibrate at a frequency equal to or greater than about three times the natural frequency of the tooth.

5. A method of cutting a tooth according to claim 3; wherein the exciting step comprises exciting the tooth to vibrate at a frequency equal to or greater than 20 kHz.

6. A method of cutting a tooth according to claim 3; wherein the controlling step comprises feeding the cutting tool in a given feed direction relative to the tooth to effect a depth of cut into the tooth which is less than the maximum amplitude of vibration of the tooth.

7. A method of cutting a tooth according to claim 6; wherein the feed direction is orthogonal to the direction of vibration of the tooth.

8. A method of cutting a tooth according to claim 3; wherein the controlling step comprises feeding the cutting tool in a given feed direction relative to the tooth at a feed rate which is less than the maximum speed of vibration of the tooth in the given direction.

9. A method of cutting a tooth according to claim 8; wherein the feed direction is the same as the direction of vibration of the tooth.

10. A method of cutting a tooth according to claim 3; wherein the controlling step comprises controlling the operation of the cutting tool to effect cutting of the tooth while maintaining the displacement thereof at a lower value than would otherwise be possible if the tooth were not vibrationally excited during the cutting thereof.

11. A method of cutting a tooth according to claim 3; wherein the controlling step comprises controlling the operation of the cutting tool to effect cutting of the tooth using a lower cutting force than would otherwise be possible if the tooth were not vibrationally excited during the cutting thereof.

* * * * *